US011877876B2

(12) United States Patent
Daley, II et al.

(10) Patent No.: US 11,877,876 B2
(45) Date of Patent: *Jan. 23, 2024

(54) DRAPE FOR AN IMAGING SYSTEM GANTRY

(71) Applicant: InSurgery, LLC, Lunenburg, MA (US)

(72) Inventors: Edward J. Daley, II, Maynard, MA (US); Russell Stanton, Lunenburg, MA (US)

(73) Assignee: InSurgery, LLC, Lunenburg, MA (US)

( * ) Notice: Subject to any disclaimer, the term of this patent is extended or adjusted under 35 U.S.C. 154(b) by 979 days.

This patent is subject to a terminal disclaimer.

(21) Appl. No.: 16/524,506

(22) Filed: Jul. 29, 2019

(65) Prior Publication Data
US 2020/0054299 A1 Feb. 20, 2020

Related U.S. Application Data

(60) Provisional application No. 62/842,167, filed on May 2, 2019, provisional application No. 62/765,266, filed on Aug. 20, 2018.

(51) Int. Cl.
A61B 46/10 (2016.01)
A61B 6/00 (2006.01)
A61B 6/03 (2006.01)

(52) U.S. Cl.
CPC ............ A61B 6/4411 (2013.01); A61B 6/032 (2013.01); A61B 6/4423 (2013.01); A61B 46/10 (2016.02)

(58) Field of Classification Search
CPC ..... A61B 6/032; A61B 6/4411; A61B 6/4423; A61B 46/10

USPC ........................................................ 128/852
See application file for complete search history.

(56) References Cited

U.S. PATENT DOCUMENTS

| 6,003,328 | A | 12/1999 | Faries, Jr. et al. |
| 8,770,839 | B2 | 7/2014 | Gregerson et al. |
| 2006/0079748 | A1 | 4/2006 | Murphy et al. |
| 2008/0216844 | A1* | 9/2008 | Olfert ............... A61B 46/10 128/856 |
| 2009/0141853 | A1* | 6/2009 | Crews ............... A61B 6/032 378/4 |
| 2011/0281064 | A1 | 11/2011 | Murphy et al. |
| 2013/0025605 | A1 | 1/2013 | Ball et al. |
| 2015/0000676 | A1 | 1/2015 | Colona |

FOREIGN PATENT DOCUMENTS

| DE | 10126465 C1 | 1/2003 |
| DE | 102010040956 A1 | 3/2012 |
| WO | 2018171720 A1 | 9/2018 |

OTHER PUBLICATIONS

Written Opinion of the International Searching Authority, dated Oct. 24, 2019 for International Application No. PCT/US2019/045280, 10 pgs.

* cited by examiner

Primary Examiner — Rafael A Ortiz
(74) Attorney, Agent, or Firm — Iandiorio Teska & Coleman, LLP

(57) ABSTRACT

An imaging system gantry patient channel drape includes a gantry first outer sidewall covering portion including an outer rim biased into a deployed (e.g., circular) shape and collapsible, and a gantry inner (e.g., circular) wall covering portion extending inward of the gantry first outer sidewall covering portion.

34 Claims, 19 Drawing Sheets

DRAPE FOR AN IMAGING SYSTEM GANTRY

RELATED APPLICATIONS

This application claims benefit of and priority to U.S. Provisional Application Ser. No. 62/765,266 filed Aug. 20, 2018 and U.S. Provisional Application Ser. No. 62/842,167 filed May 2, 2019, under 35 U.S.C. §§ 19, 120, 363, 365, and 37 C.F.R. § 1.55 and § 1.78, which are incorporated herein by this reference.

FIELD OF THE INVENTION

This subject invention relates to drapes protecting the gantry of an imaging system such as a computerized tomography (CT) machine to establish a sterile barrier to protect the patient and to drape to create a protective barrier for other uses and applications (e.g., a masks used in painting operations).

BACKGROUND OF THE INVENTION

Imaging systems such as computerized tomography (CT) machines are often used during surgery. A typical CT machine (e.g., the Mobius Imaging, LLC "Airo" product) includes a gantry with a patient channel therethrough mounted to a gimbal itself mounted to a base. The gimbal can be moved linearly relative to the base. The base also includes a column supporting a patient table which can be moved linearly with respect to the column in and out of the gantry patient channel. See, for example, U.S. Pat. No. 8,770,839 incorporated herein by this reference.

Sterility, of course, is extremely important in the operating theater. If a physician or nurse even touches a non-sterile surface or item, the health care professional must then leave the operating room, rescrub, and don new operating room attire. The CT gantry is considered non-sterile. Breaking sterility can result in increased time and cost associated with surgery.

Accordingly, sterile drapes for imaging machines have been developed. For example, U.S. Published Patent Application No. 2011/0281064 (incorporated herein by this reference) discloses a drape for the patient channel of an imaging machine. The drape is in a form of a sleeve with elastic bands about each opening which are stretched over lips at the patient channel openings of the machine. See also WO2018/0171720 incorporated herein by this reference.

BRIEF SUMMARY OF THE INVENTION

Still, in some cases, no lips are provided on the gantry. And, it can be difficult and time consuming to deploy drapes without breaking sterility. In some cases, it was so difficult to apply a drape to the gantry that hospital staff "double draped" a patient instead. This is done by having a secondary sterile drape flaked back and ready for each scan. Just prior to the scan, the second drape is unfolded over the patient, clipped carefully so as not to come in contact with the gantry patient channel, and the scan is then taken. Then, after the scan, the secondary drape is carefully flaked back out of the way to be ready for the next scan.

Featured is a new imaging system gantry patient channel drape which is fast and easy to deploy, fast and easy to remove, and which can be manufacturing inexpensively.

One preferred imaging system gantry patient channel drape includes a gantry first outer sidewall covering portion including an outer rim biased into a deployed (e.g., circular) shape and collapsible, a gantry inner (e.g., circular) wall covering portion extending inward of the gantry first outer sidewall covering portion, and a plurality of stays connectable to the gantry.

In one embodiment, the plurality of stays extend from the gantry circular wall covering portion. The drape may further include a gantry second outer sidewall covering portion extending from the gantry inner circular wall covering portion. The stays then typically extend from the gantry second outer sidewall covering portion. The drape may further include means for removably attaching the gantry first outer sidewall covering portion to the first outer gantry sidewall. In one version, these means includes Velcro patches on the gantry first outer sidewall covering portion and corresponding Velcro patches on the first outer gantry sidewall. The drape may further include means for removably attaching the stays to the second outer gantry sidewall. In one version, the means for removably attaching the stays to the second outer gantry sidewall include a Velcro patch on each stay and corresponding Velcro patches on the second outer gantry sidewall. The drape may further include sleeves on the stays and/or sleeves on the gantry first outer sidewall covering portion.

The drape may further include a stay holder removably attached to the stays to prevent the stays from contacting the gantry during installation of the drape. In one version, the stay holder is removably attached to the stays via Velcro on the stays and Velcro on the stay holder. The drape stay holder is preferably ring shaped.

Also featured is a method of protecting an imaging system gantry patient channel. The method may include un-packaging a gantry drape including a gantry first outer sidewall covering portion with an outer rim biased into a deployed shape, a gantry inner wall covering portion extending inward of the gantry first outer sidewall covering portion, and a plurality of stays attached to the drape. The gantry first outer sidewall covering portion is secured to a first gantry outer sidewall and the gantry inner wall covering portion is drawn to cover the gantry patient channel wall. The stays may be secured to a second outer gantry sidewall.

Securing the gantry first outer sidewall covering portion to the first gantry outer sidewall may include securing Velcro patches on the gantry first outer sidewall covering portion to Velcro patches on the first outer gantry sidewall Securing the stays to the second outer gantry sidewall may include securing Velcro patches on the stays to Velcro patches on the second outer gantry sidewall. Securing the gantry first outer sidewall covering portion to the first gantry outer sidewall may include employing sleeves located on the gantry first outer sidewall covering portion. Securing the stays to the gantry second outer sideway may include employing sleeves on the stays. Securing the gantry inner wall covering portion to the gantry patient channel wall may include drawing a stay holder removably attached to the stays through the patient channel of the gantry. Attaching the plurality of stays to the gantry second outer sidewall may include removing the stays from the stay holder.

Also featured is a drape comprising a first outer sidewall covering portion including an outer rim biased into a deployed shape and collapsible, an inner wall covering portion extending inward of the first outer sidewall covering portion, and a plurality of stays.

The plurality of stays may extend inward from the inner wall covering portion. In one version, a second outer sidewall covering portion extending from the inner wall covering portion and the stays extend from the second outer sidewall covering portion.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
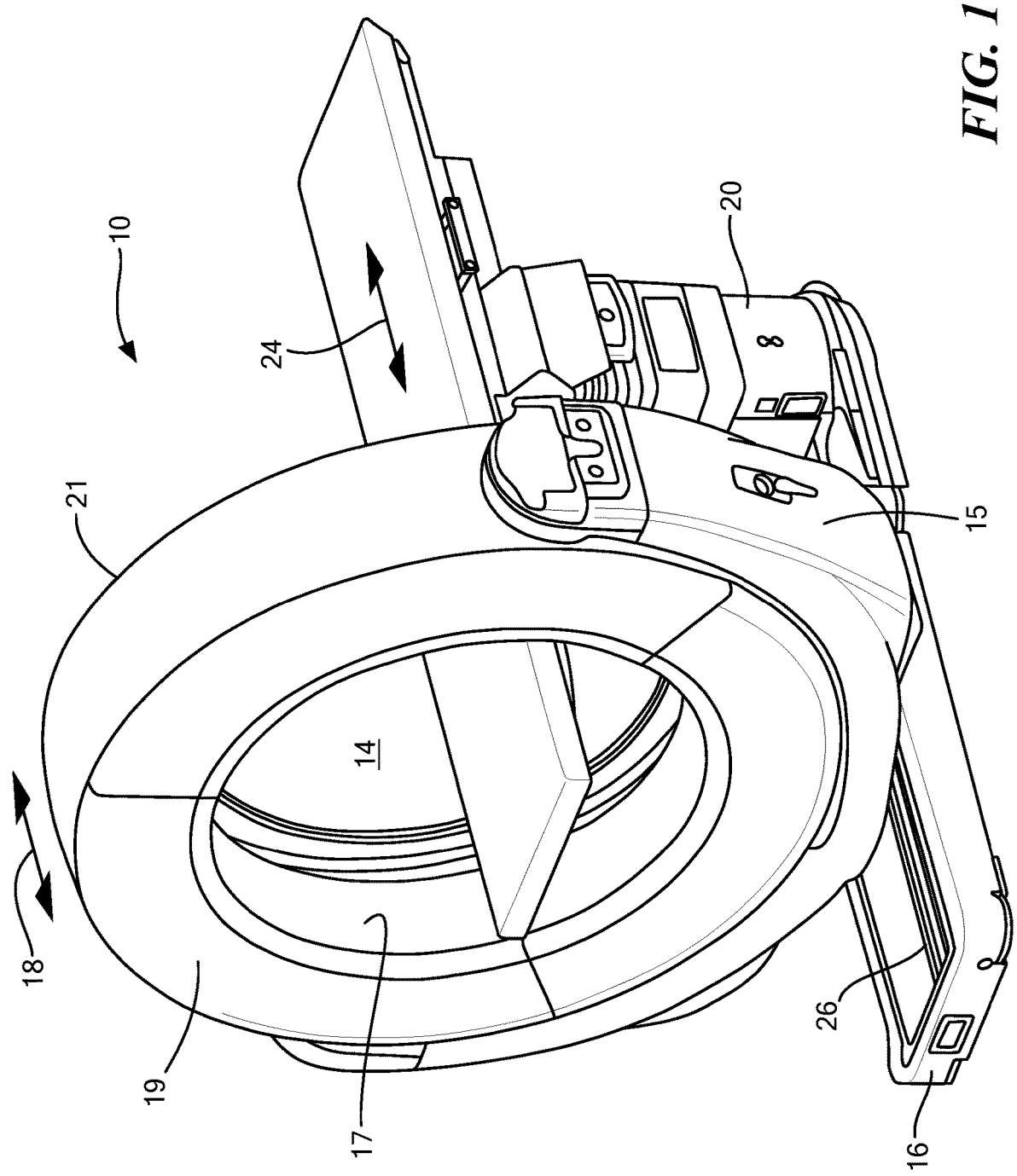
FIG. 1 is a schematic three dimensional view of an example of an imaging system.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 shows an example of an imaging system 10 used in an operating room. Gantry 12 defines patient channel 14 and is mounted to gimbal 15 which moves relative to base 16 in the direction shown by arrow 18. Base 16 also supports column 20 supporting patient table 22 which moves relative to column 20 in the direction shown by arrow 24.

Figure 2:
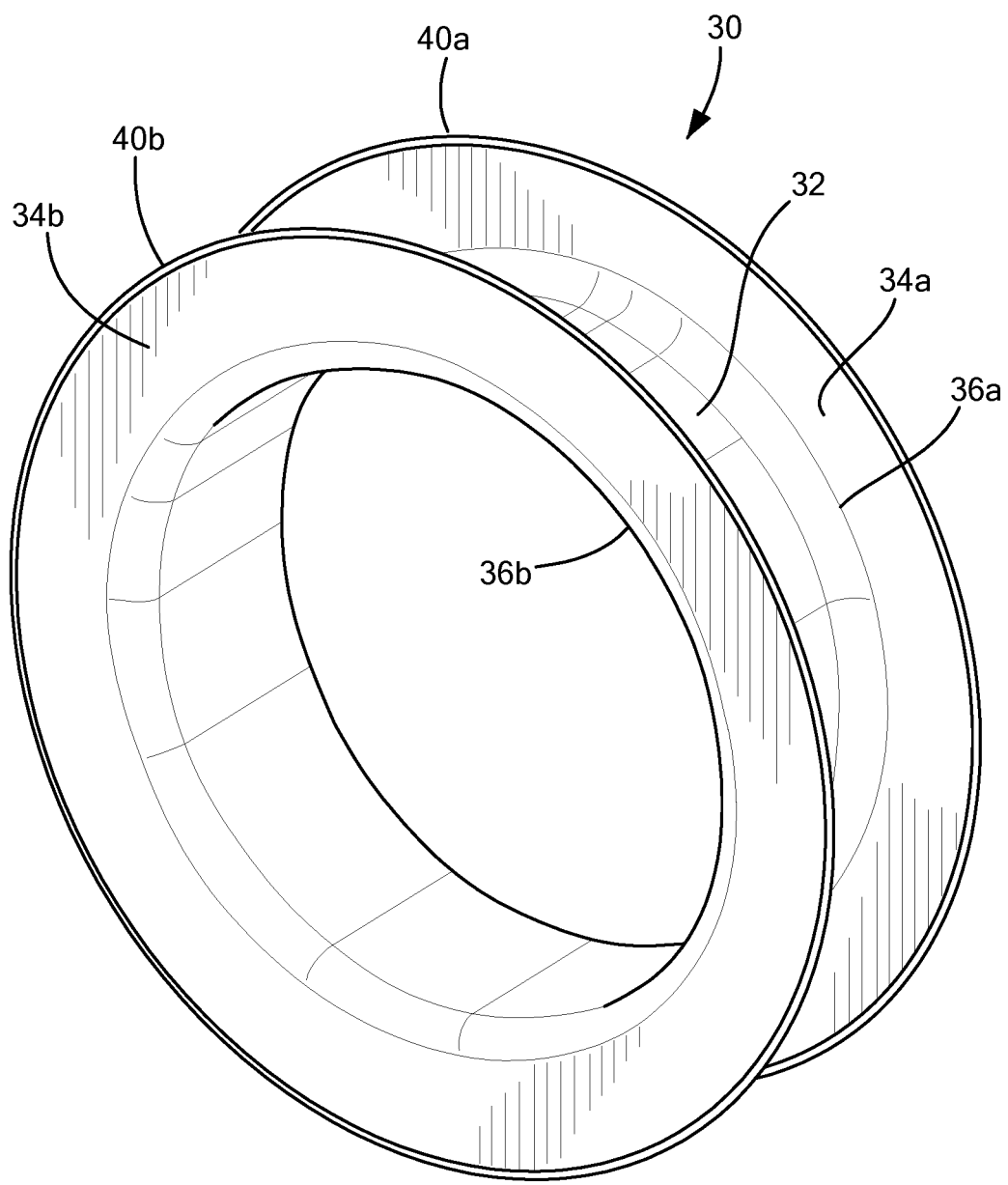
FIG. 2 is a schematic view showing one embodiment of a drape for the gantry of the imaging system shown in FIG. 1.

FIG. 2 depicts one version of an imaging system gantry patient channel drape 30 with gantry inner (e.g., circular) wall covering portion 32 which contacts and covers the inner circular wall 17, FIG. 1 of the gantry defining the patient channel. Gantry outside wall covering portion 34a extends outwardly from edge 36a of covering portion 32 and gantry outside wall covering portion 34b extends outwardly from the opposite edge 36b of covering portion 32. These outer sidewall covering portions cover all or in some other cases only a small portion of the gantry sidewalls, e.g., sidewall 19 and 21, FIG. 1. The covering portions need not be uniformly round.

There are preferably means for biasing one or both outer sidewall covering portions into the deployed (e.g., circular) shape shown in FIG. 2. In one example, such means includes spring members (e.g., bands) 40a, 40b associated with outer sidewall covering portions 34a, 34 respectively. Each spring band may be attached to the outer periphery of each covering portion or reside in a sleeve or channel at the periphery of the covering portion. Each spring band is preferably flexible in order to package the drape but also has a memory automatically urging the spring band back into a hoop shape when released from the packaging. Various shape memory alloys are known in the art. The drape thus self-deploys.

Figure 3:
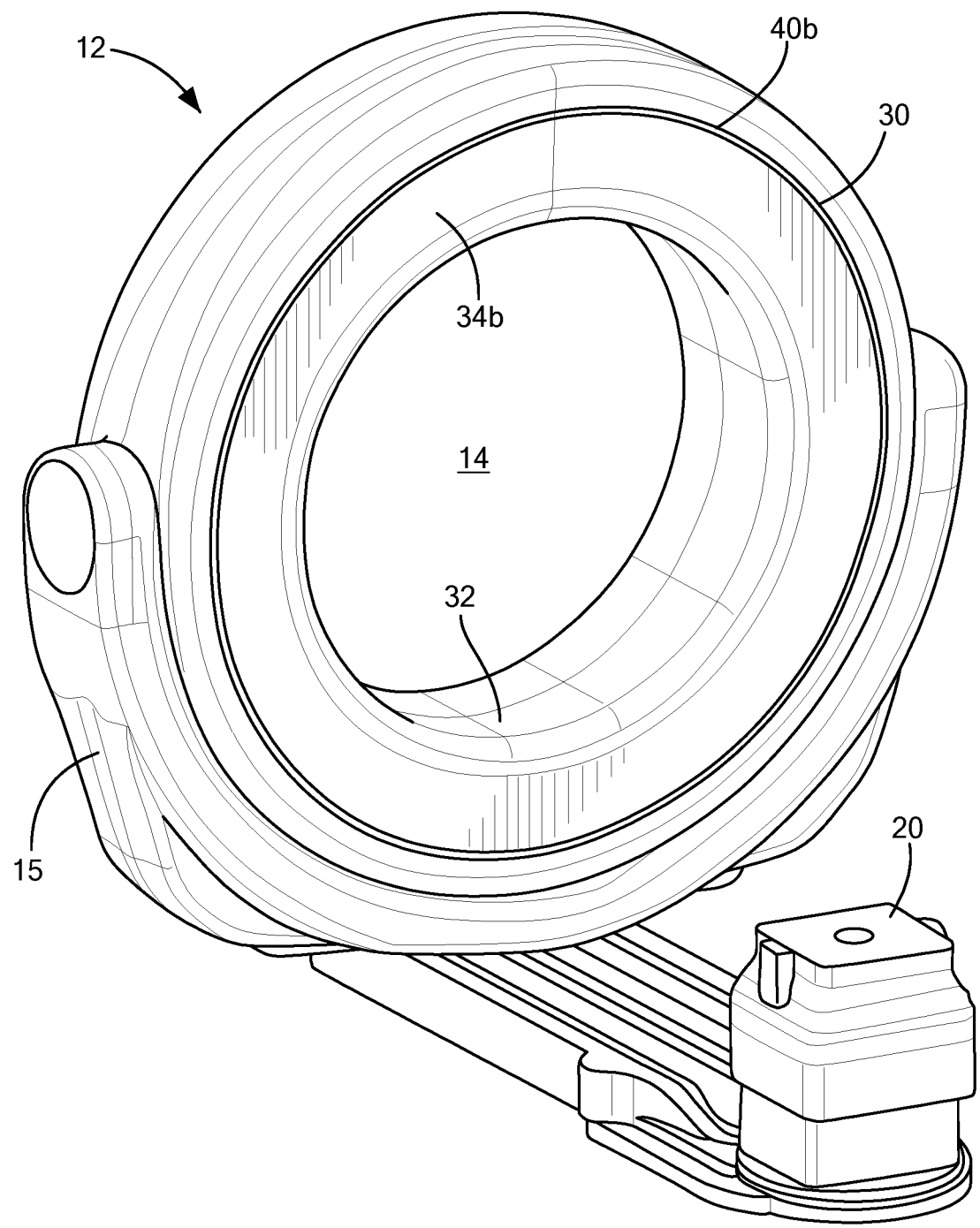
FIG. 3 is a schematic view showing the drape of FIG. 2 protecting the gantry of an imaging machine.

As shown in FIG. 3, when drape 30 is unpackaged and deployed, the spring bands return to their hoop shape urging drape inner circular wall covering portion 32 about the gantry inner circular wall and urging the outer sidewall coverings to cover all or at least a portion of the outer sidewalls of the gantry.

Figure 4:
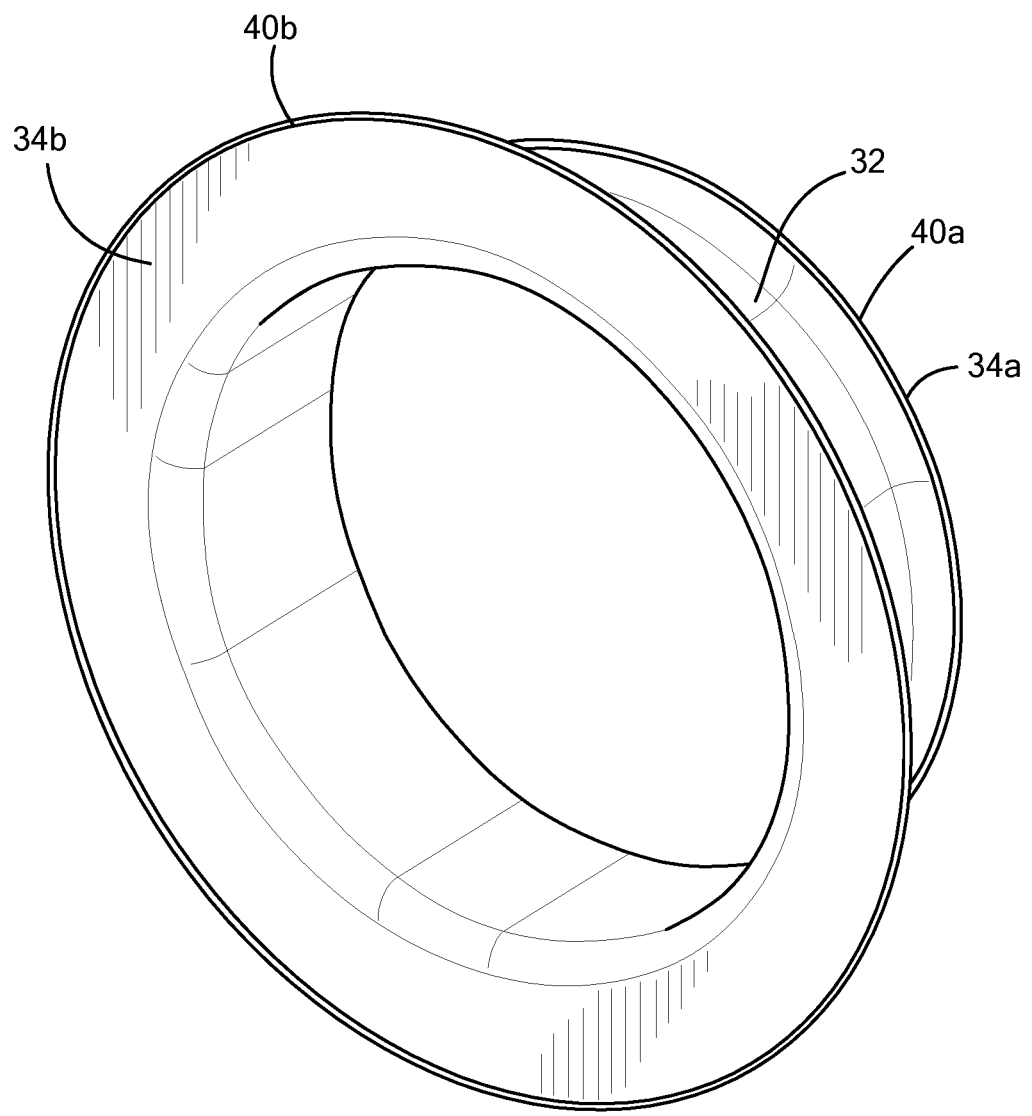
FIG. 4 is a schematic view showing another version of a gantry drape.
Figure 5B:
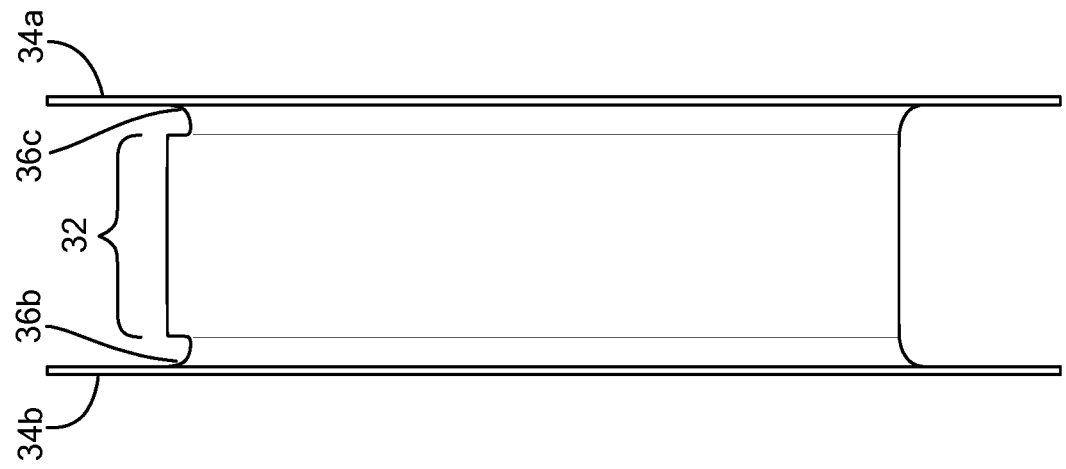
FIGS. 5A-6B are schematic views showing still other embodiments of a gantry drape.
Figure 5A:
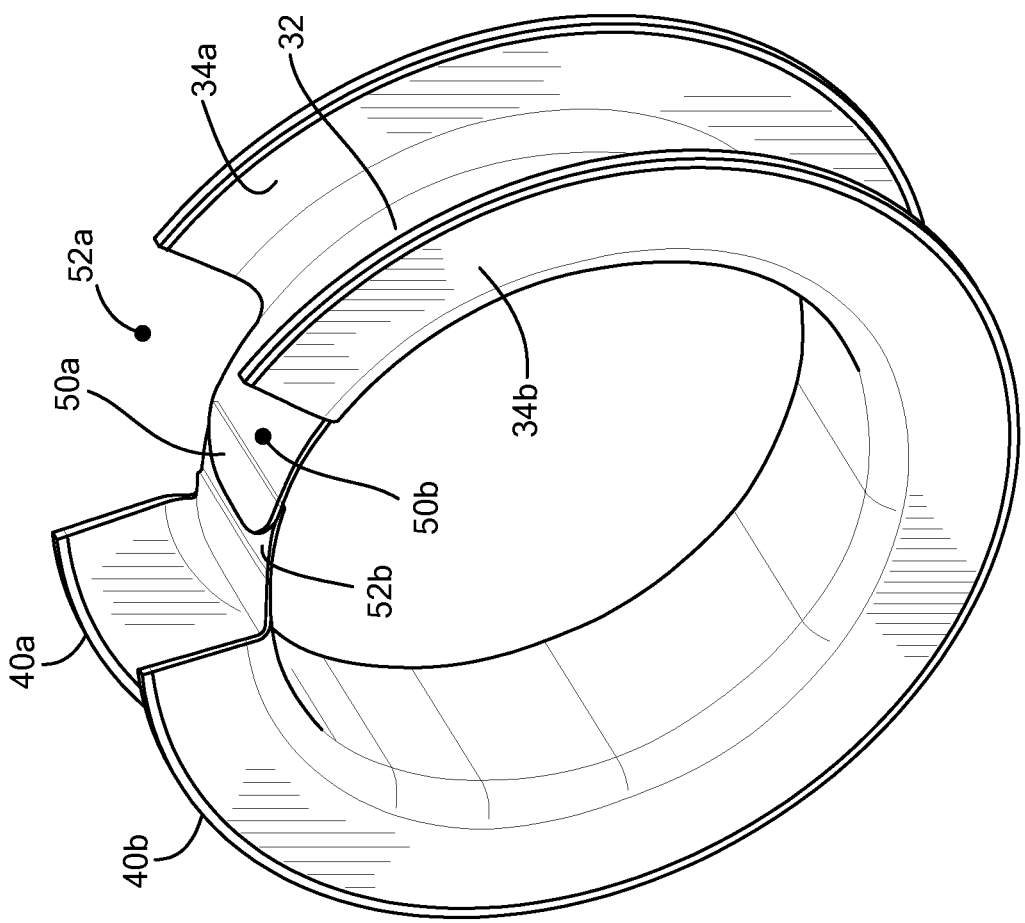
Figure 6B:
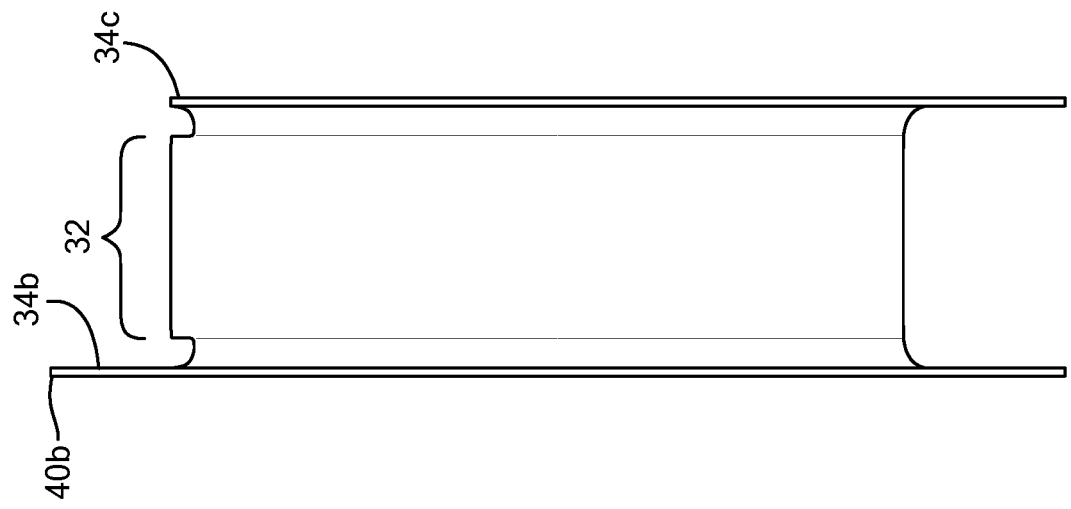
Figure 6A:
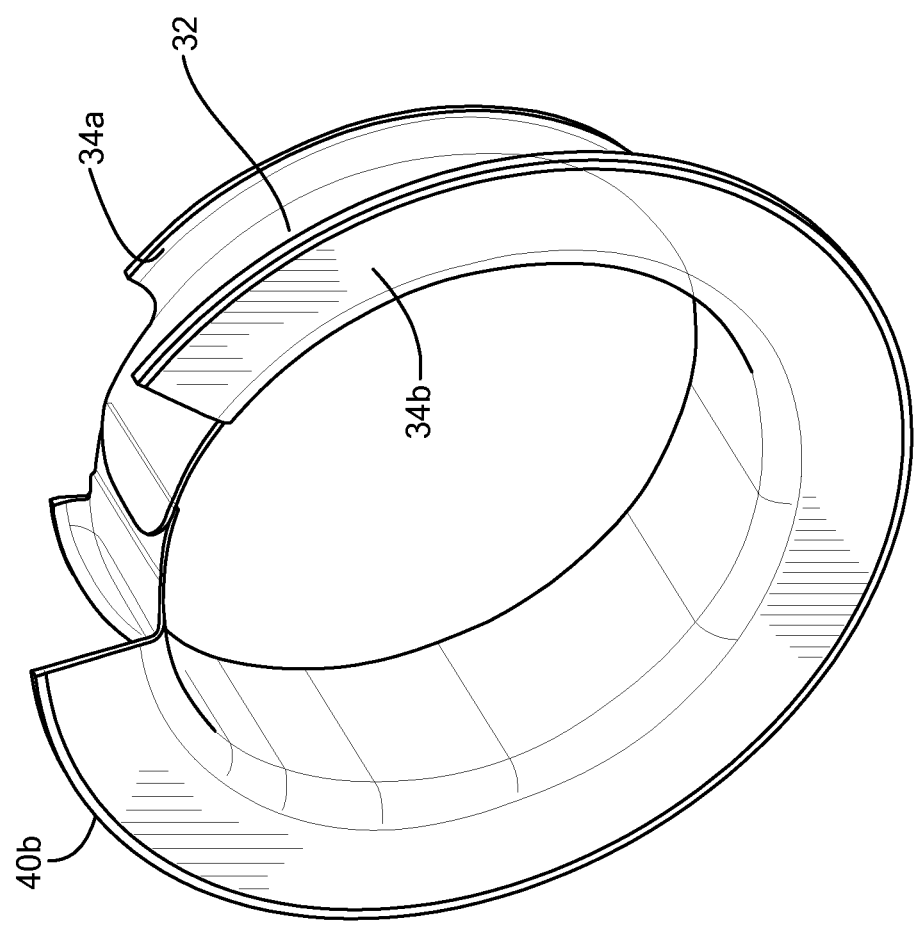

In some embodiments, the one or more outer covering portions do not extend outwardly as far as shown in the FIG. 2. See FIG. 4. In some embodiments, the inner wall covering portion is continuous as shown in FIG. 2 (e.g., a complete one piece cylinder). In other embodiments, this covering portion is discontinuous as shown in FIGS. 5A-5B where portion 32 includes first and second end portions 50a, 50b which may overlap as shown and are secured to each other or to the inside wall 17, FIG. 1 of the gantry. Adhesive, Velcro, or other fasteners may be used. Also, in some embodiments, the outer gantry wall covering portions include cutout sections as shown at 52a, 52b for portions 34a, 34b, respectively. In this way, any sensors associated with the gantry sidewalls are not covered by the drape. In some cases, the spring members 40a, 40b may be complete loops or in other cases only partial loops in structure. In some embodiments, there is a spring member 40b associated with only one outer gantry wall covering portion as shown in FIG. 6.

Figure 7:
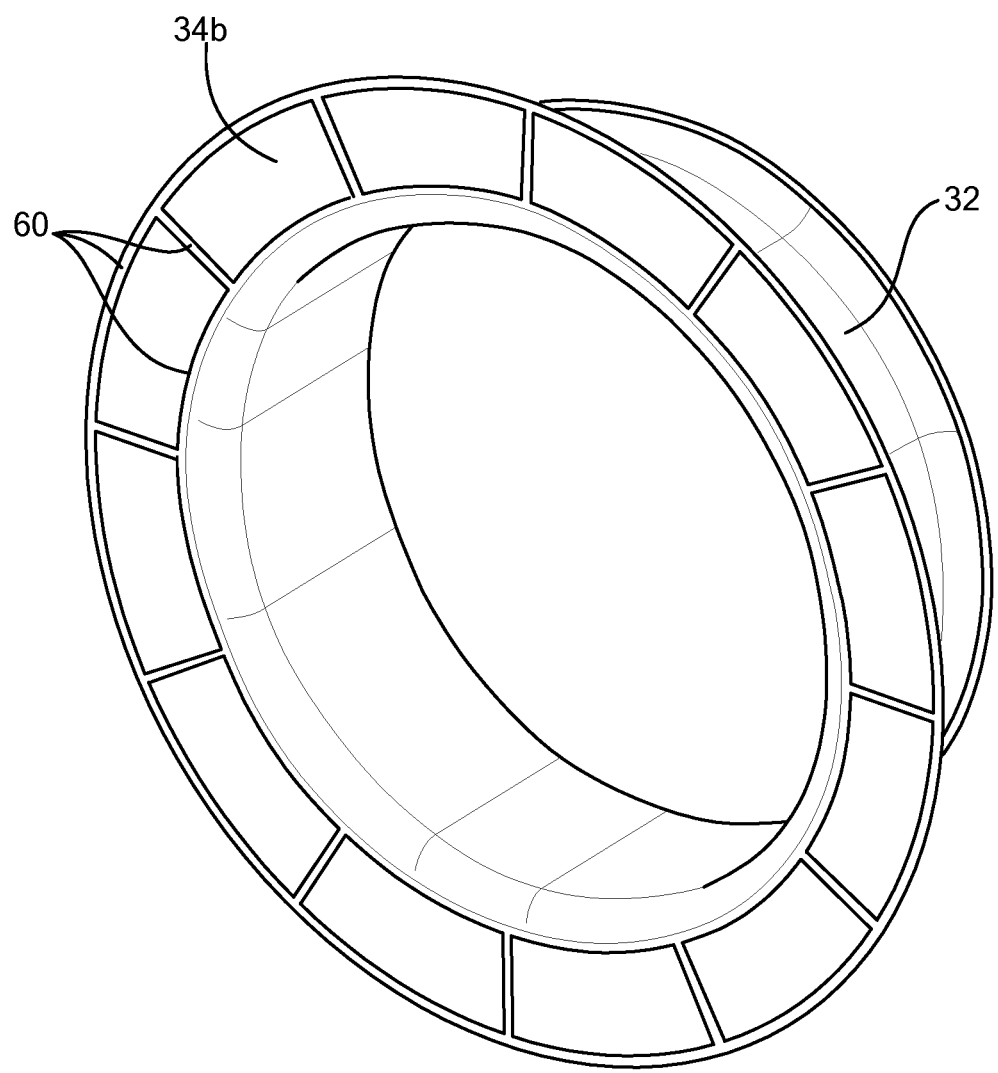
FIG. 7 is a schematic view showing how a series of inflated bladders bias the drape into a position which protects the patient channel of the gantry.
Figure 8A:
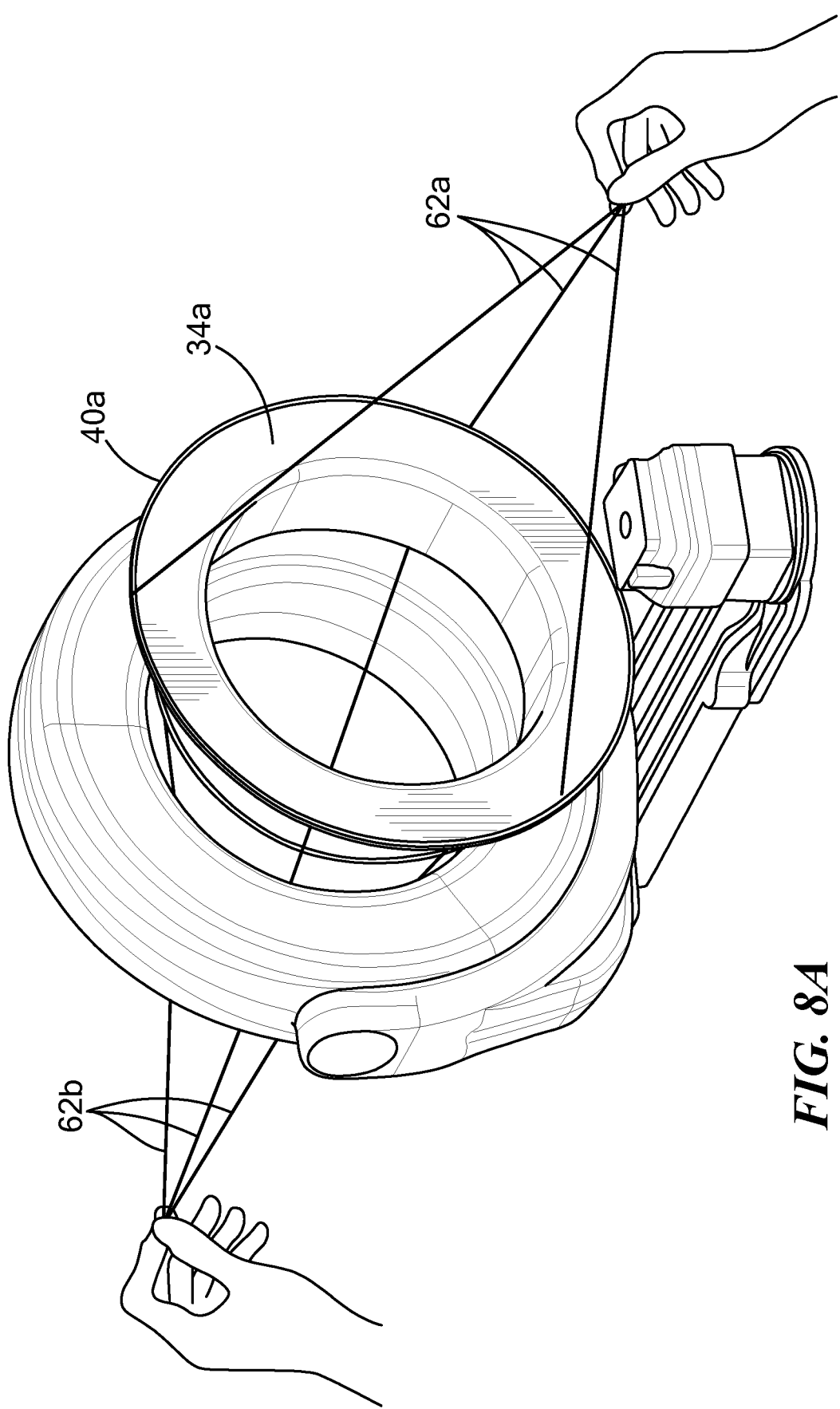
FIGS. 8A-8C are schematic views showing one method of deploying the drapes shown in FIGS. 2 and 4.
Figure 8B:
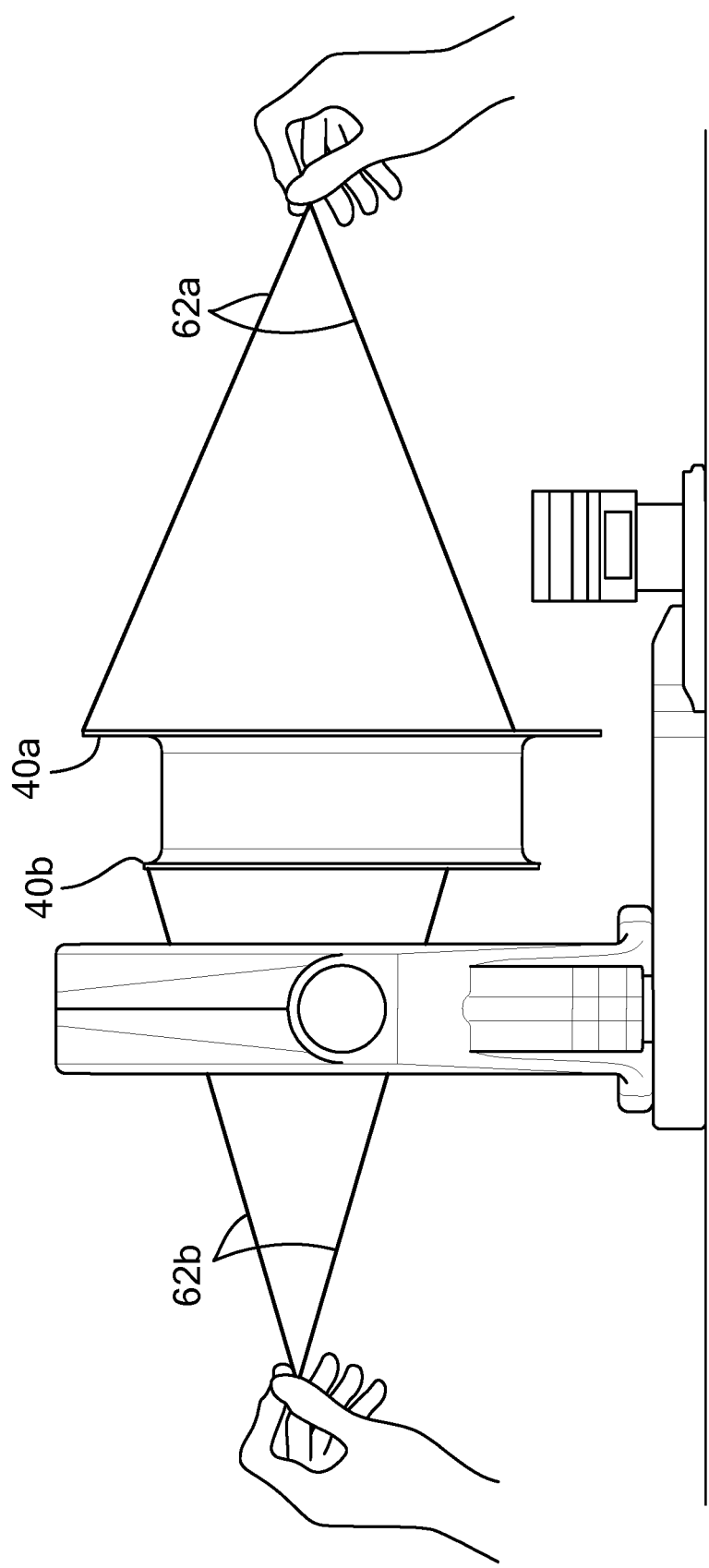
Figure 8C:
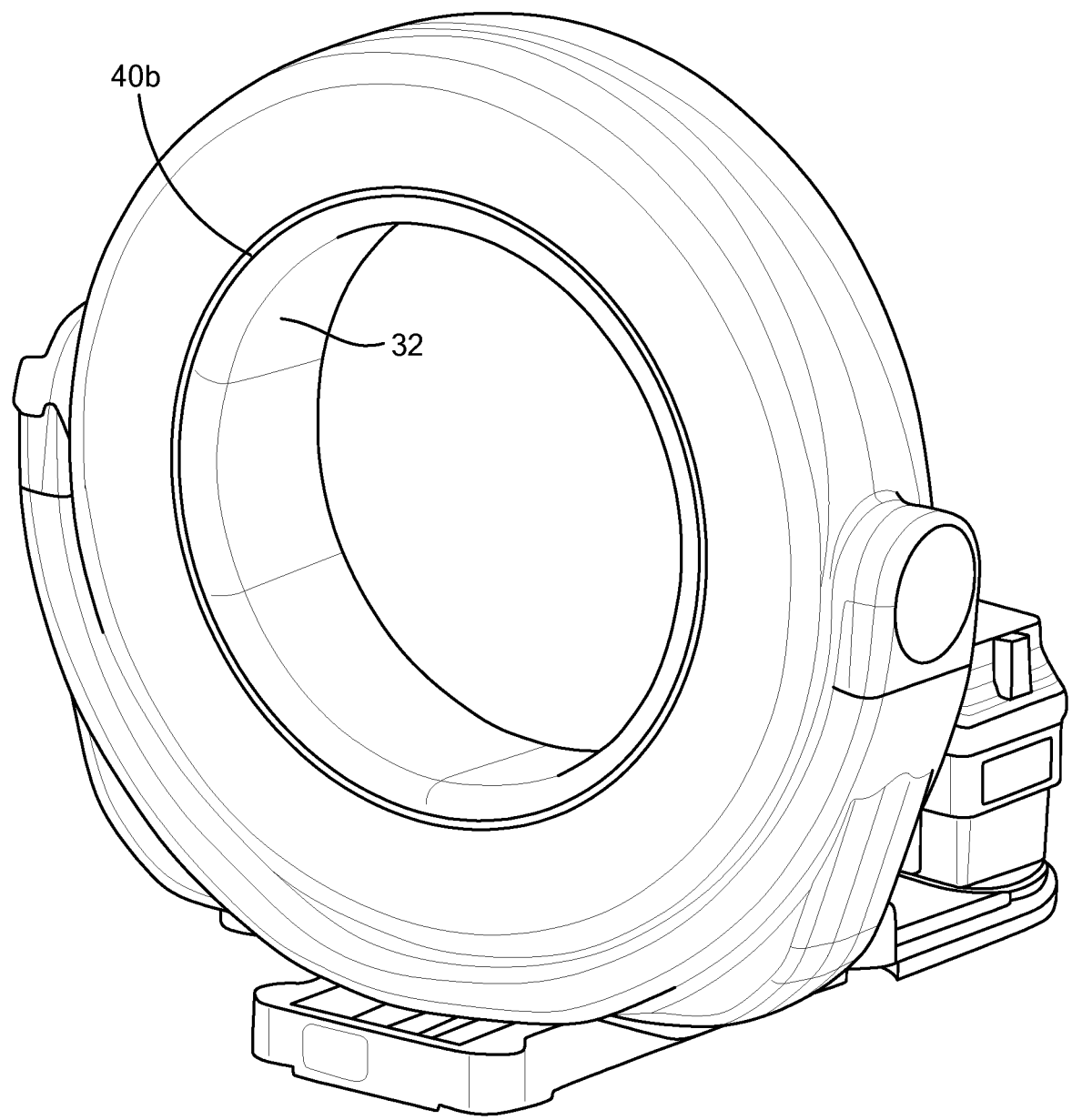

In the embodiment of FIG. 7, the means for biasing includes inflatable bladders 60 associated with one or more outer gantry wall coverings. Such air bag drapes are inflated in the patient channel or bore of the imaging device. Inflation can be achieved with a disposable pressurized canister, pump, or the pressurized air lines available in many operating rooms. To deploy such a drape it is removed from a sterile outer packaging and placed in the lowest part of the imaging of the gantry patient channel diameter. The inflatable bladders are inflated and as the drape inflates it is guided into place taking care that non-sterile items do not contaminate the sterile portions of the drape (if any). If needed, secondary fixation devices such as adhesive, Velcro, hooks, male/female connectors, does, static cling, and the like can be used. 62 are attached to the spring members and are used to deploy, for example, the drape of FIG. 4. Again, the drape is removed from a sterile outer packaging and the cords attached to the drape are passed through the patient imaging channel. As the ends of the cords are pulled away from each other the spring members in the drape will untwist and unfold and hold its deployed shape. The drape may be secured to the imaging system with adhesive or mechanical means (if needed).

The spring members used can be metal or nonmetal (e.g., for magnetic resonance applications). And, in some cases, as noted above, the drapes may employ a secondary fixation device such as adhesive, Velcro, hooks, male/female connectors, docks, static cling, or the like (to completely secure the drape to the gantry). The drape may be made of plastic sheeting, for example, LDPE (Low Density Polyethylene). The drape could be either sterile or non-sterile.

Figure 9:
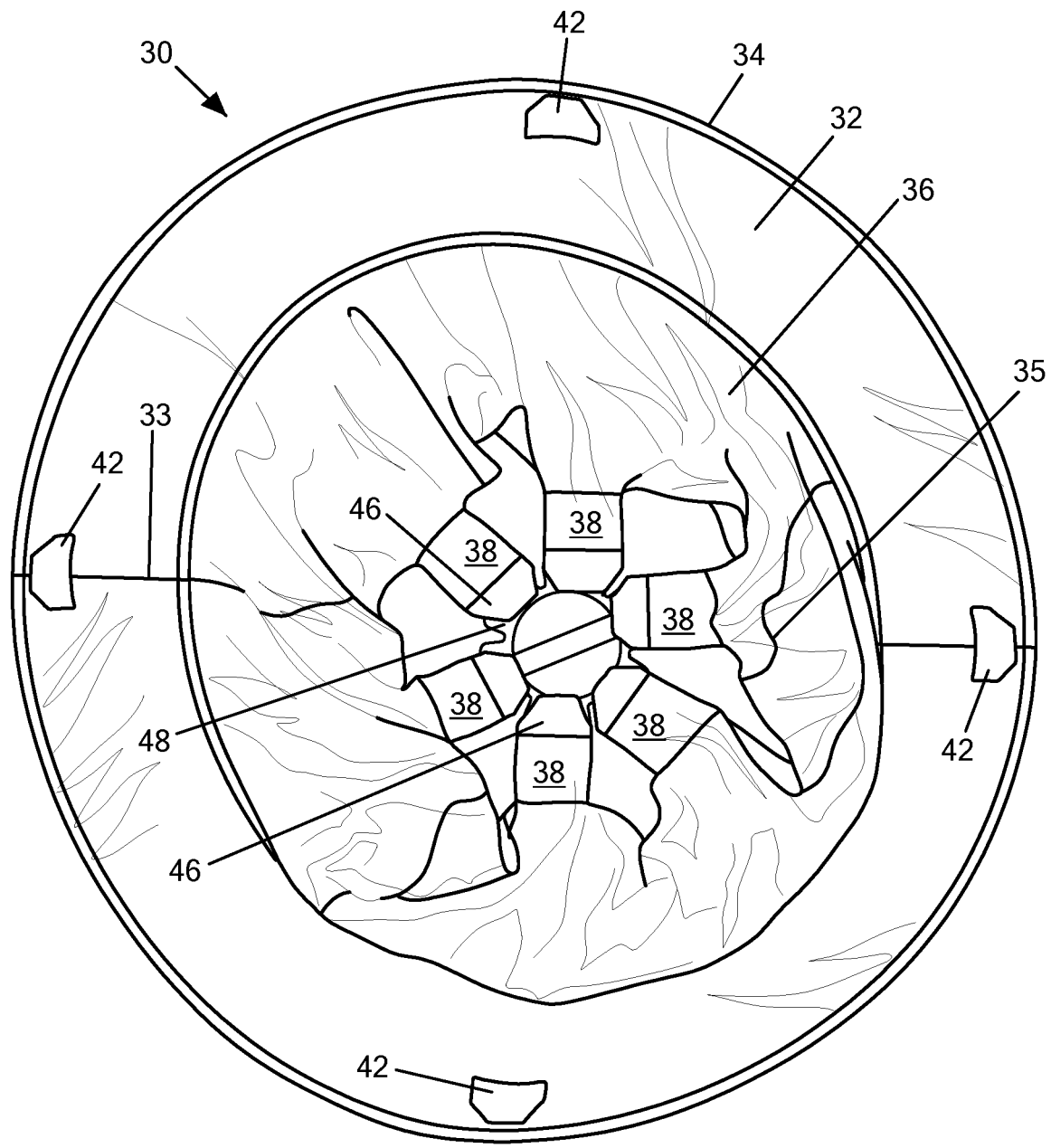
FIG. 9 is a schematic view showing an embodiment of a drape for the gantry of the imaging system shown in FIG. 1.
Figure 10:
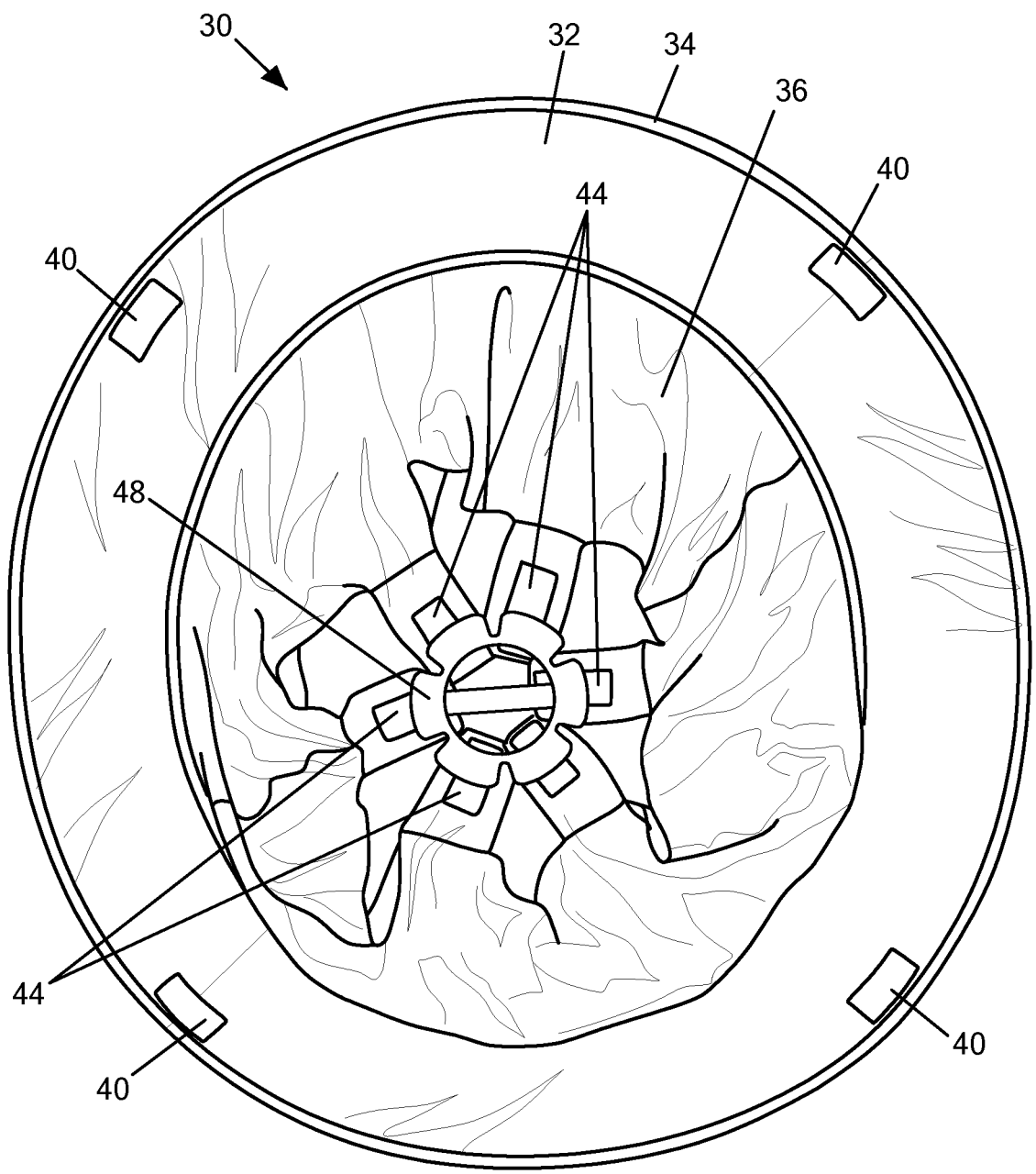
FIG. 10 is a schematic view showing the rear of the drape of FIG. 9.
Figure 14:
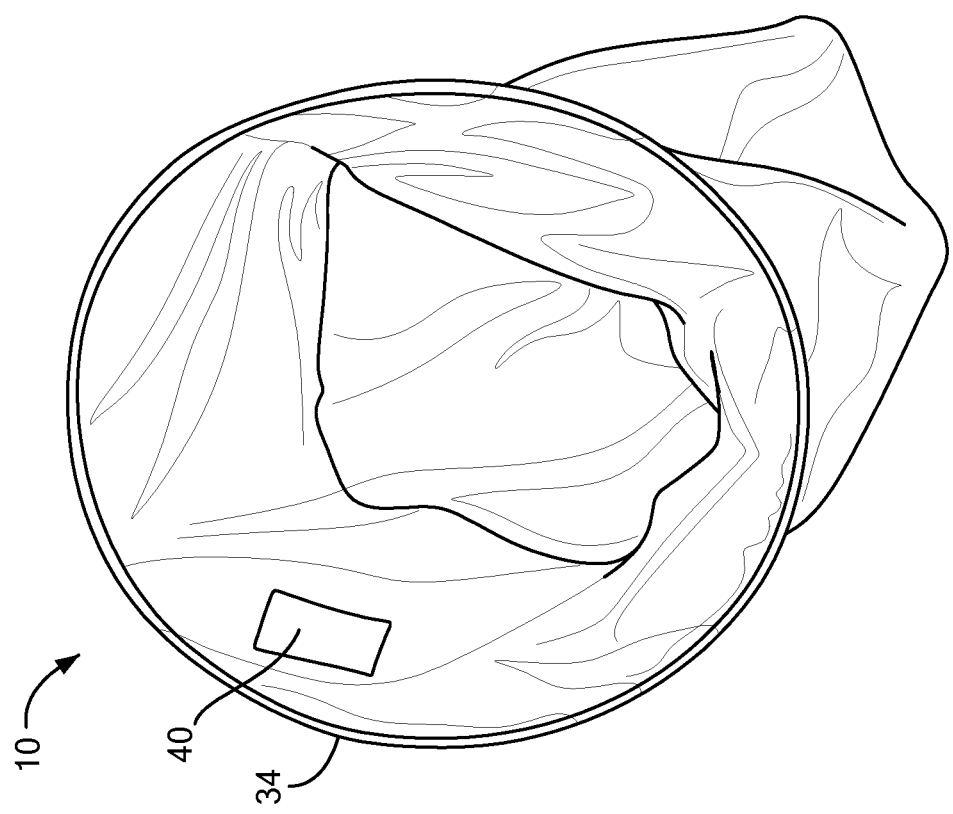
FIG. 14 is a view showing the drape in its folded configuration.

FIGS. 9-10 depict another example of imaging system gantry patient channel drape 30 including a gantry first outer sidewall covering portion 32 biased into the circular shape shown in FIGS. 9 and 10 via spring member 34 and yet also collapsible as shown in FIG. 14. The spring member may be a band attached to the outer periphery of the gantry first outer sidewall covering portion 32 and reside in a sleeve or a channel at the periphery thereof. Each spring band is flexible in order to package the drape but also has a memory urging the spring band back into a hoop shape when released from the packaging. Various shape memory alloys are known in the art.

Figure 12:
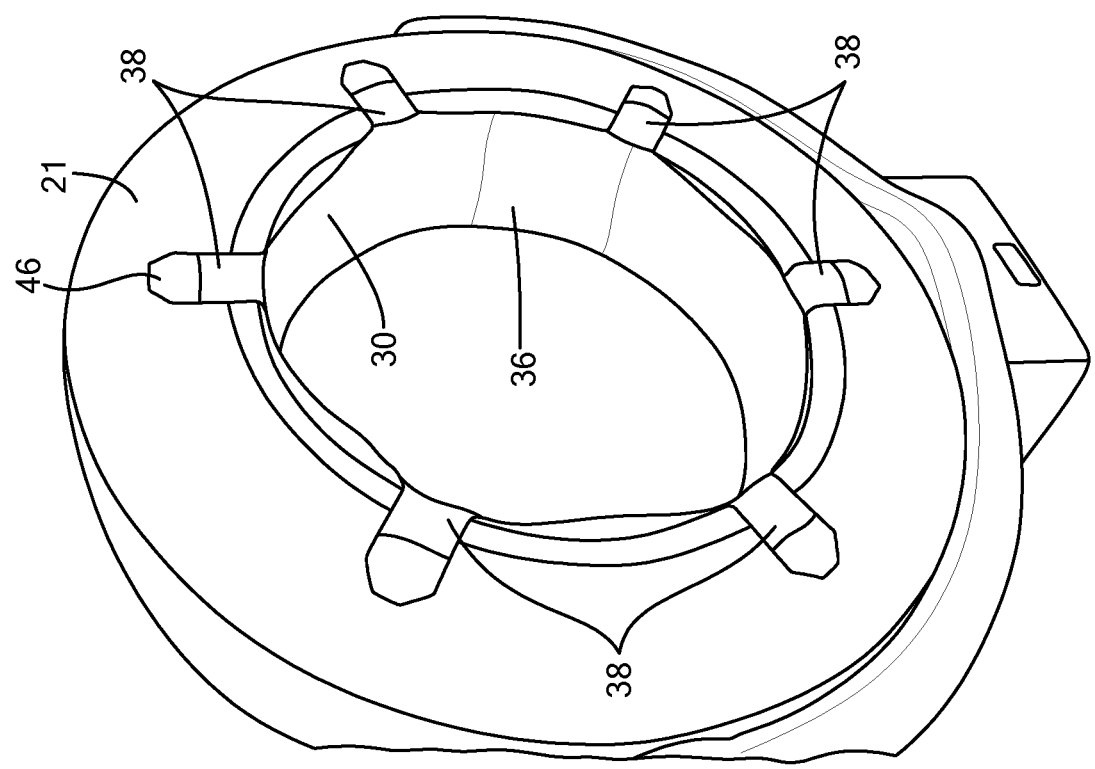
FIG. 12 is a view showing the rear of the gantry of FIG. 11.
Figure 11:
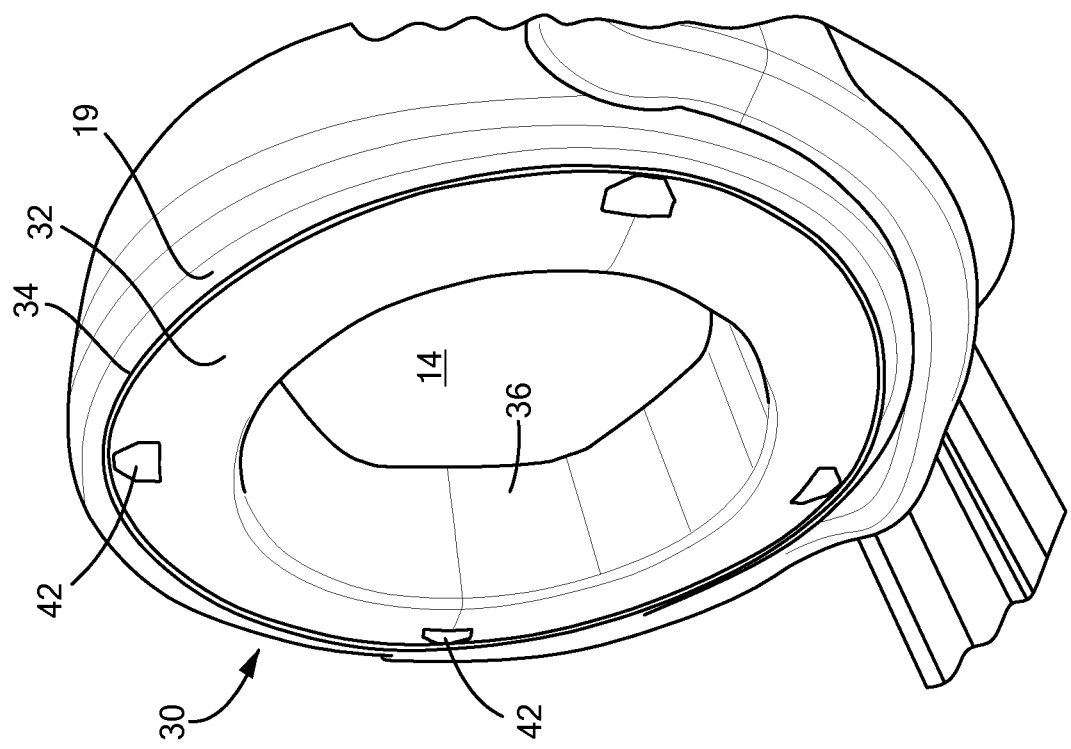
FIG. 11 is a schematic view showing the drape of FIGS. 9-10 protecting the gantry of an imaging machine.

Gantry first outer sidewall covering portion 32 (with one or more seams 33) covers one sidewall 19 or substantially covers one sidewall of the gantry as shown in FIGS. 11-12. Gantry inner circular wall covering portion 36 extends inward of gantry first outer sidewall covering portion 32 and, as shown, covers the gantry inner circular wall 17, FIG. 1. Portion 36 may include one or more seams 35. A plurality of drape stays 38 are removably connectable to the gantry. In the particular embodiment shown in FIGS. 9-10, and 12, the plurality of stays 38 are located inward of the gantry inner circular wall covering portion 36 and are releasably attachable to the second gantry outer sidewall 21 as shown in FIG. 12.

Preferably, further included are means for removably attaching the gantry first outer sidewall covering portion 32 to the first outer gantry sidewall 19 such as Velcro patches 40, FIG. 9 secured to the inside of the gantry first outer sidewall covering portion 32 proximate the periphery thereof. A corresponding set of Velcro patches are attached to the first outer gantry sidewall 19, FIG. 1. Opposite the inner Velcro patches or at some other location, the outside of the gantry first outer sidewall covering portion 32 may include built in hand sleeves 42, FIGS. 10 and 11, to prevent the user from accidently touching any non-sterile surfaces. The sleeves or handholds help avoid user contamination.

The drape further may include means for removably attaching the stays 38 to the second outer gantry sidewall 21 such as a Velcro patch 44 on each stay and corresponding Velcro patches attached to gantry second outer sidewall 21. And, the stays may each include a sleeve 46 opposite the stay Velcro patches again to prevent the user from accidently touching any non-sterile surfaces.

Stay holder or keeper 48, FIG. 9 is removably attached to the stays 38 preferably via Velcro on the stay holder to prevent the stays 38 from contacting the gantry during installation of the drape. Stay keeper 48 is preferably ring shaped as shown. The stay keeper helps avoid contamination of the drape and/or patient.

The result is a gantry patient channel drape that preserves sterility and also protects any electronics associated with the gantry. The drape is folded and packaged. The user then removes the drape from its package and allows the drape to unfold as biased rim 34 returns to a circular or other shape. Sleeves 42 are then used to attach the gantry first outer sidewall covering portion 32 to the gantry first outer sidewall 19. Stay keeper 48 is then brought through the patient channel of the gantry so that gantry inner circular wall covering portion 36 covers and protects the gantry inner circular wall. Then, one by one, the stays 38 are removed from the stay keeper 48 and secured to the gantry second outer sidewall 21 as shown in FIG. 12. The drape can be installed in less than one minute and after surgery easily removed from the gantry and refolded to be placed in its packaging for disposal.

Figure 13:
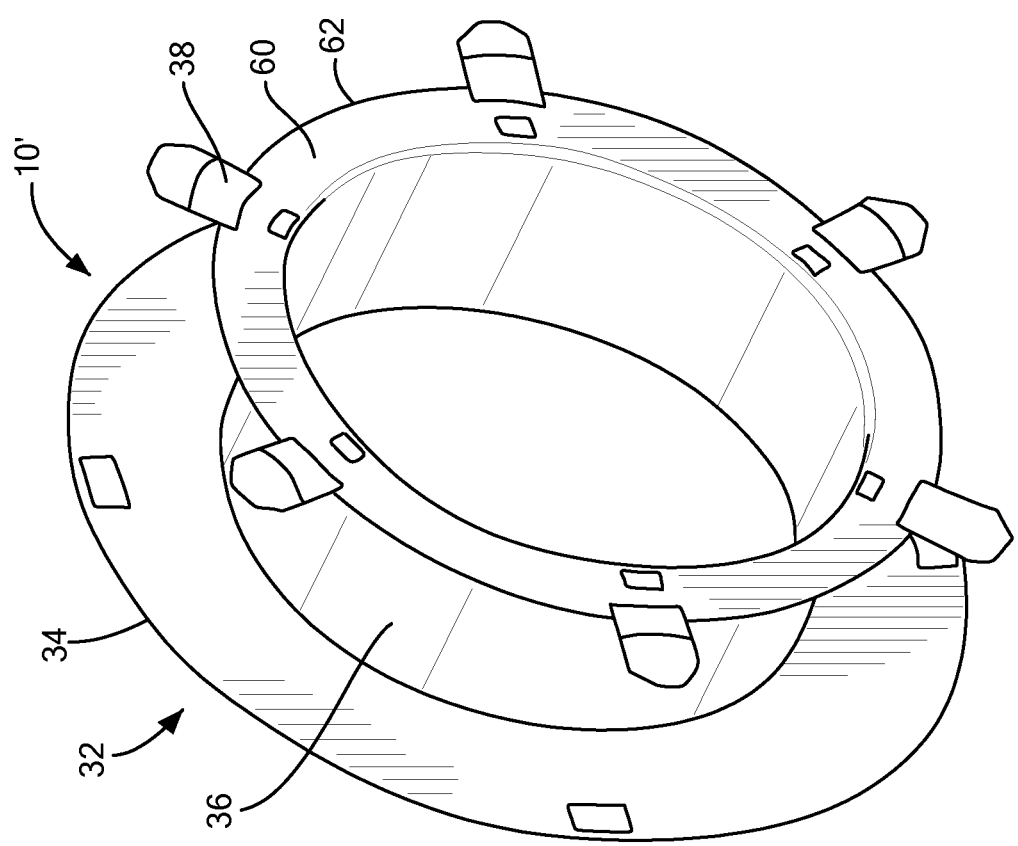
FIG. 13 is a schematic view showing another version of a gantry drape.

FIG. 13 shows a version where the drape includes gantry first outer sidewall covering portion 32 with a rim 34 biased into a circular shape and collapsible, gantry inner circular wall covering portion 36, and gantry second outer sidewall covering portion 60 with stays 38. Covering portion 60 may be as large or smaller than portion 32 and may include a rim 62 biased into a circular shape and also collapsible. The result is a gantry drape which is easy and quick to install and which prevents anyone in the operating theater from breaking sterility Other draft/gantry fixation devices include adhesives, hooks, male/female connectors, static cling, and the like. The spring members used can be metal or nonmetal (e.g., for magnetic resonance applications). And, in some cases, as noted above, the drapes may employ a secondary fixation device such as adhesive, Velcro, hooks, male/female connectors, docks, static cling, or the like (to completely secure the drape to the gantry). The drape may be made of plastic sheeting, for example, LDPE (Low Density Polyethylene). The drape could be either sterile or non-sterile.

Figure 15:
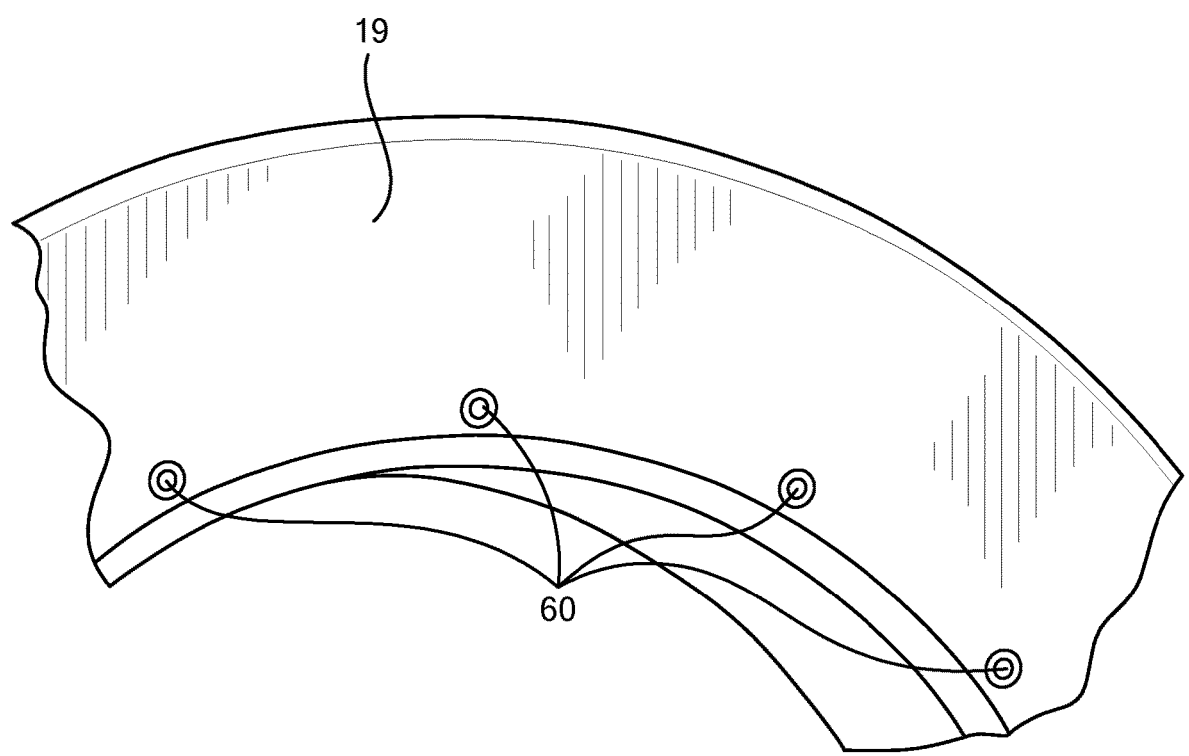
FIG. 15 shows a gantry with navigation markers.
Figure 16B:
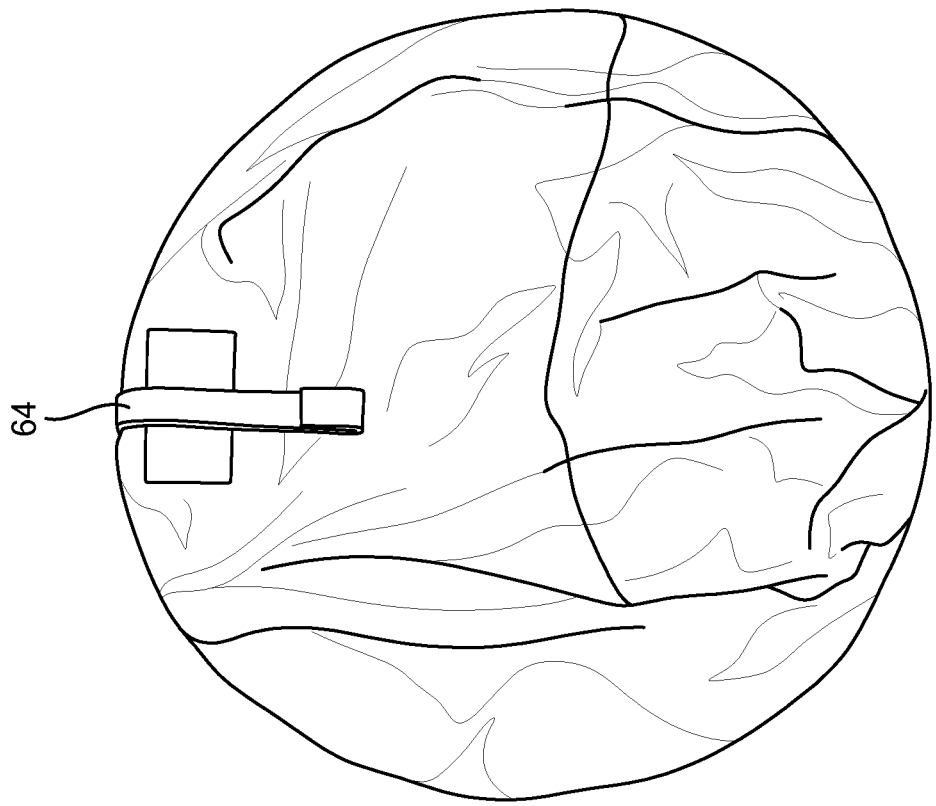
FIGS. 16A-16D show a drape closure strap.
Figure 16A:
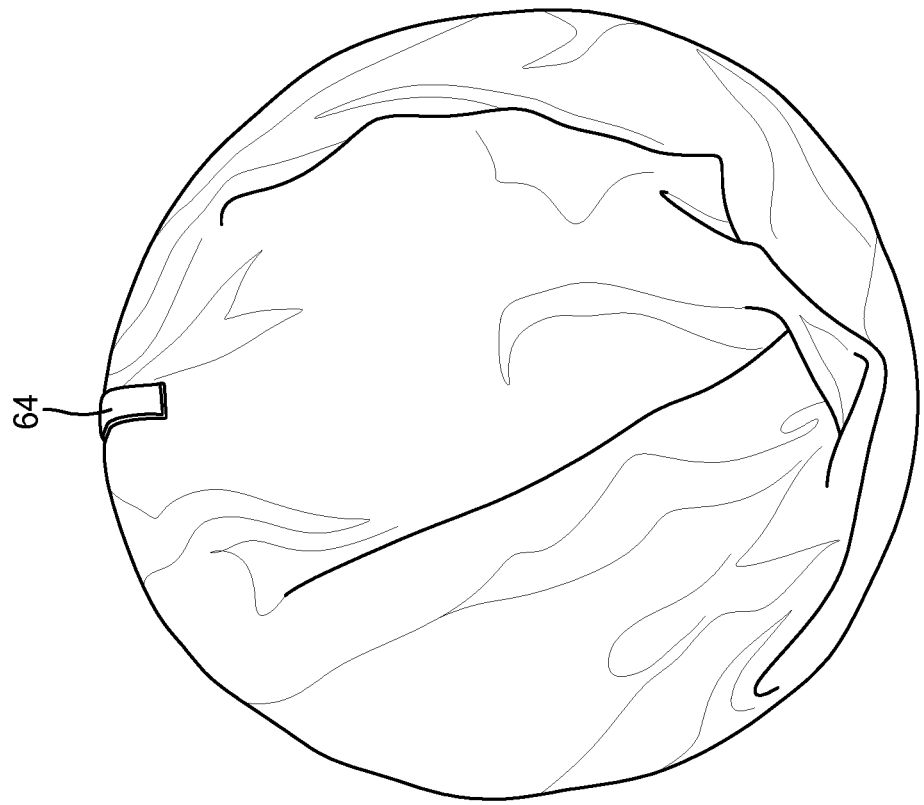
Figure 16C:
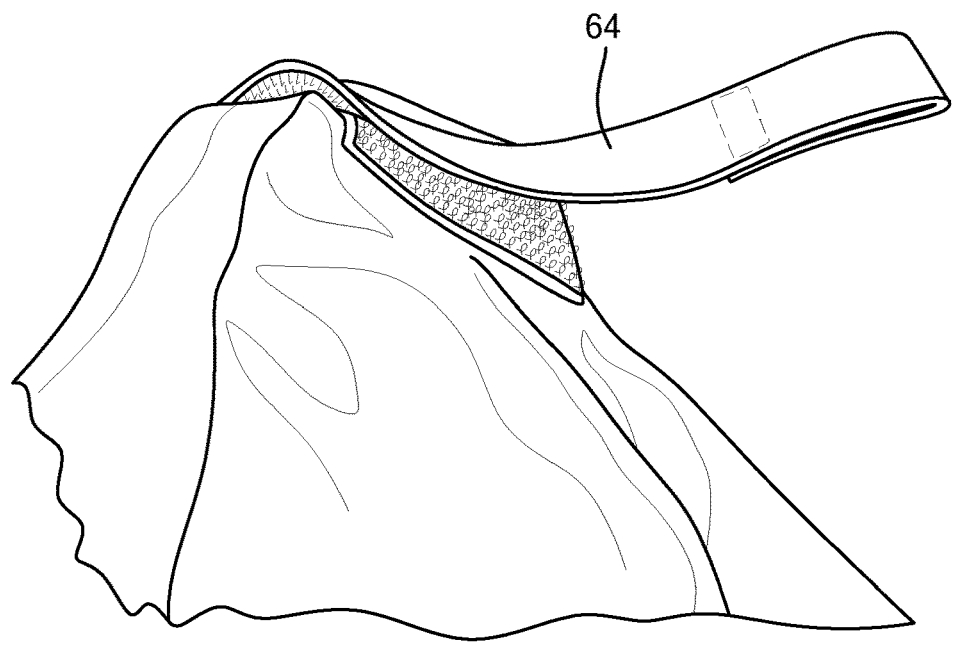
Figure 16D:
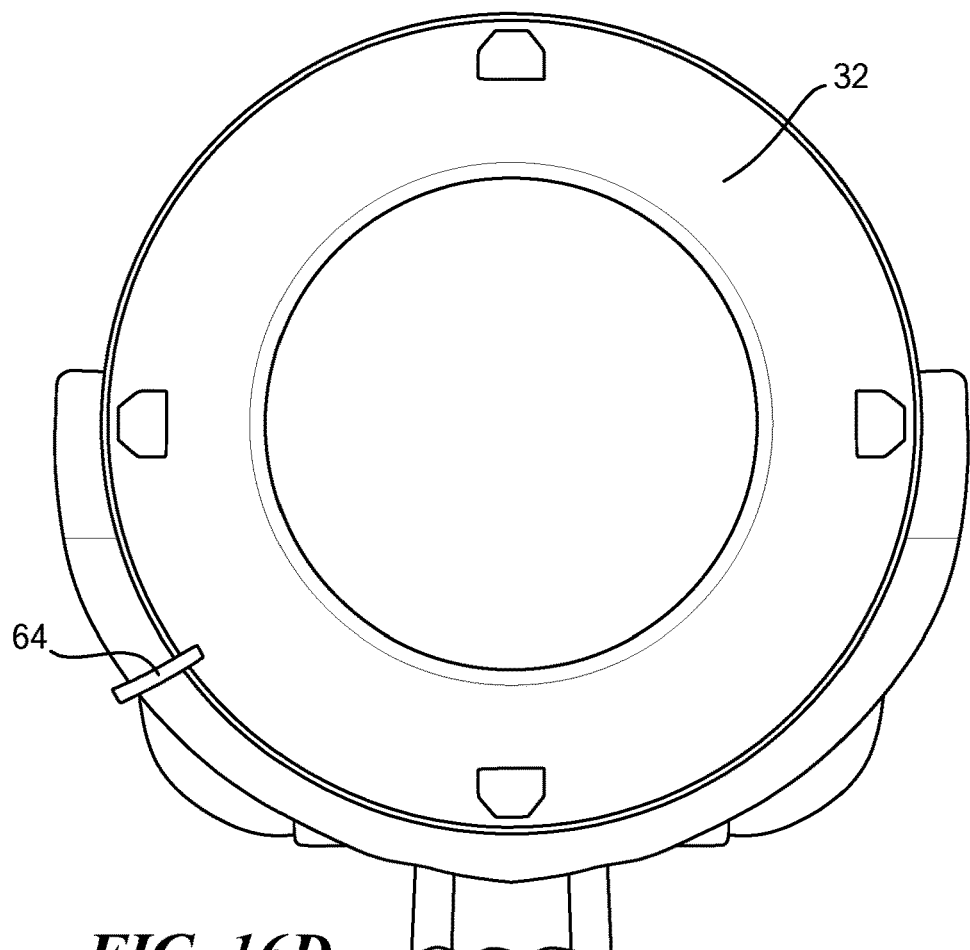

FIG. 15 shows a gantry sidewall 19 with navigation markers 60. Thus, the drape may include windows or openings corresponding to the location of markers 60 to ensure the markers 60 are not blocked occluded.

FIGS. 16A-16D show a closure strap 64 used when deploying the drape. The closure strap is attached to the outside of sidewall covering portion 32 to keep the drape coiled flat and can be releasably attached (e.g., via Velcro) to the inside of sidewall covering portion 32. When the drape is coiled properly, the inside and outside surfaces of the first sidewall will oppose each other. The coiling action rotates these faces so they oppose each other. So, a closure strap can make contact with both faces. Also, the orientation of the closure strap below waist height (approximately at "8 o'clock" in this version) was intentional, as typically anything below waist height in the operating room is considered a non-sterile region. So, when the drape is installed on the machine, this strap, that could freely move and make unintentional contact with a non-sterile surface, will be below the region a scrubbed staff member practicing sterile protocol would intentionally reach.

Figure 17A:
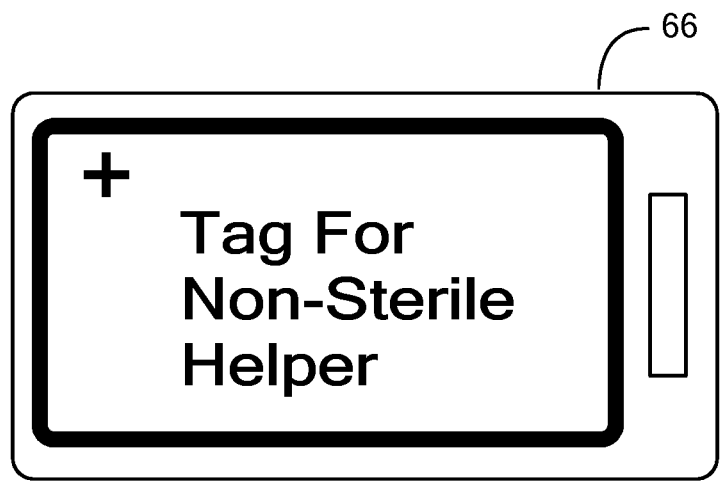
FIGS. 17A-17C show a tear away tag associated with the drape.
Figure 17B:
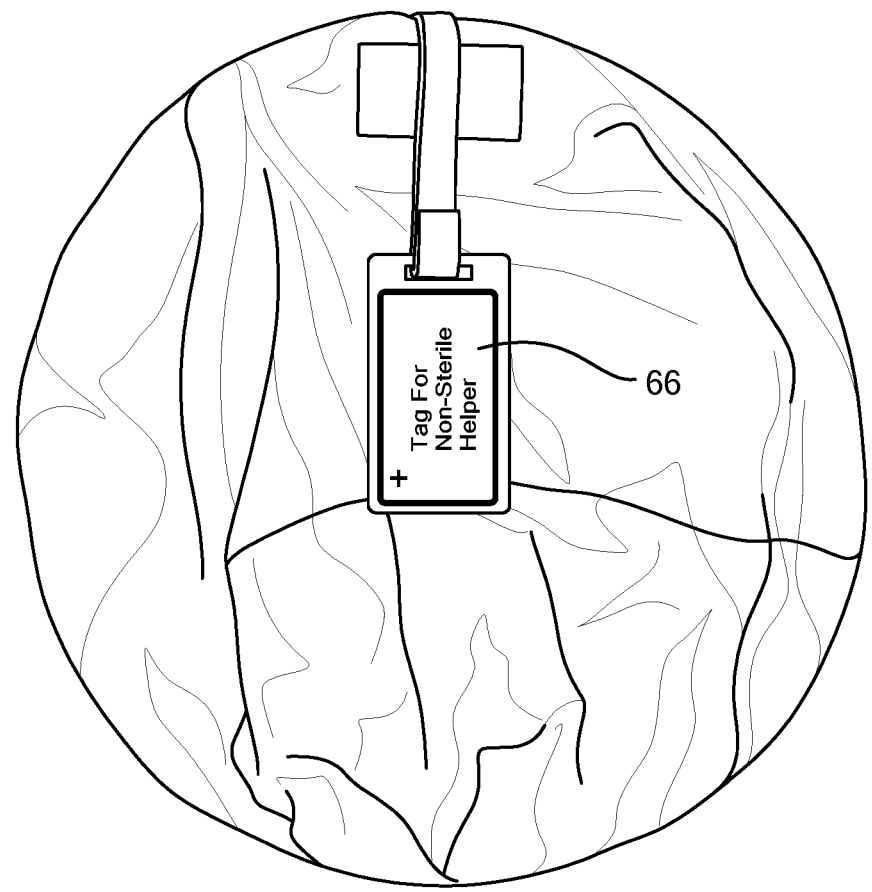
Figure 17C:
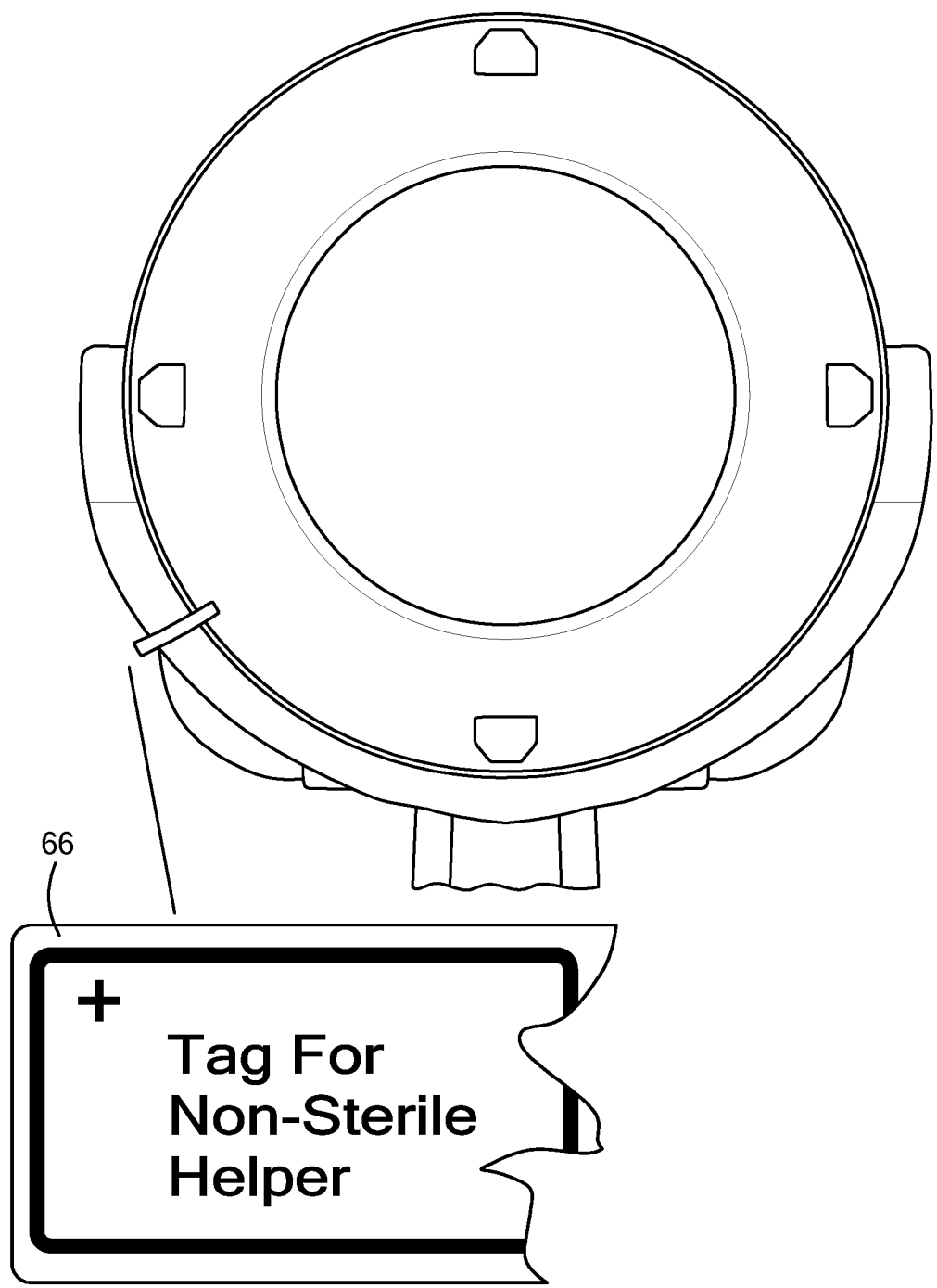

FIG. 17A depicts a sterile tear away tag (66) not attached to the drape. FIG. 17B depicts a sterile tear away tag (66) attached to closure strap prior to installation (64) FIG. 17C depicts the drape installed on the imaging device, with the sterile tear away tag (66) removed. The sterile tear away tag workflow has been employed as a long-established common practice for donning sterile gowns. It allows a non-sterile staff member to make contact with a sterile item (a gown) in a way that doesn't contaminate the entire item (gown). Because the non-sterile staff member's contact contaminates the tag, it is purposely made to be town away after use.

The Gantry Drape can deploy quickly and is large in size, so it may be helpful, especially for shorter staff members to get assistance from other staff to control deployment and installation of the drape. The ability to employ the aid of non-sterile staff members is very helpful.

Although specific features of the invention are shown in some drawings and not in others, however, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims. For example, the drape could be used in other applications (e.g., masking in paint operations) in the aerospace, agriculture, manufacturing, food industry, and other industries. For example, the drape can be applied to jet engines during manufacturing, testing, or in use of the aircraft, for example, to prevent birds and other contaminants from entering the jet engine when the aircraft is parked.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

What is claimed is:

1. An imaging system gantry patient channel drape comprising:
   a gantry first outer sidewall covering portion including an outer rim biased into a deployed shape and collapsible;
   a gantry inner wall covering portion extending inward of the gantry first outer sidewall covering portion;
   a plurality of stays connectable to the gantry and securing the drape to the gantry and sleeves on the stays; and
   a stay holder removably attached to the stays to prevent the stays from contacting the gantry during installation of the drape.

2. The drape of claim 1 in which the plurality of stays extend from the gantry inner wall covering portion.

3. The drape of claim 1 in which the one or more stays include a gantry second outer sidewall covering portion extending from the gantry inner wall covering portion.

4. The drape of claim 3 in which the gantry second outer sidewall covering portion includes an outer rim biased into a deployed shape and collapsible.

5. The drape of claim 1 further including means for removably attaching the gantry first outer sidewall covering portion to a first outer gantry sidewall.

6. The drape of claim 5 in which said means includes Velcro patches on the gantry first outer sidewall covering portion and corresponding Velcro patches on the first outer gantry sidewall.

7. The drape of claim 1 further including means for removably attaching the stays to a second outer gantry sidewall.

8. The drape of claim 7 in which the means for removably attaching the stays to the second outer gantry sidewall include a Velcro patch on each stay and corresponding Velcro patches on the second outer gantry sidewall.

9. The drape of claim 1 further including additional sleeves on the gantry first outer sidewall covering portion.

10. The drape of claim 1 in which the stay holder is removably attached to the stays via Velcro on the stays and Velcro on the stay holder.

11. The drape of claim 1 in which the stay holder is ring shaped.

12. An imaging system gantry patient channel drape comprising:
    a gantry first outer sidewall covering portion including sleeves thereon and an outer rim biased into a deployed shape and collapsible;
    a gantry inner wall covering portion extending inward of the gantry first outer sidewall covering portion;
    one or more fixation devices including a plurality of stays connectable to the gantry securing the drape to the gantry; and
    a stay holder removably attached to the stays to prevent the stays from contacting the gantry during installation of the drape.

13. The drape of claim 12 in which the plurality of stays extend from the gantry inner wall covering portion.

14. The drape of claim 12 in which the one or more fixation devices include a gantry second outer sidewall covering portion extending from the gantry inner wall covering portion.

15. The drape of claim 14 in which the gantry second outer sidewall covering portion includes an outer rim biased into a deployed shape and collapsible.

16. The drape of claim 12 further including means for removably attaching the gantry first outer sidewall covering portion to a first outer gantry sidewall.

17. The drape of claim 16 in which said means includes Velcro patches on the gantry first outer sidewall covering portion and corresponding Velcro patches on the first outer gantry sidewall.

18. The drape of claim 12 further including means for removably attaching the stays to a second outer gantry sidewall.

19. The drape of claim 18 in which the means for removably attaching the stays to the second outer gantry sidewall include a Velcro patch on each stay and corresponding Velcro patches on the second outer gantry sidewall.

20. The drape of claim 12 further including additional sleeves on the stays.

21. The drape of claim 12 in which the stay holder is removably attached to the stays via Velcro on the stays and Velcro on the stay holder.

22. The drape of claim 12 in which the stay holder is ring shaped.

23. An imaging system gantry patient channel drape comprising:
    a gantry first outer sidewall covering portion including an outer rim biased into a deployed shape and collapsible;
    a gantry inner wall covering portion extending inward of the gantry first outer sidewall covering portion;
    a plurality of stays connectable to the gantry and securing the drape to the gantry; and
    a stay holder removably attached to the stays to prevent the stays from contacting the gantry during installation of the drape.

24. The drape of claim 23 in which the plurality of stays extend from the gantry inner wall covering portion.

25. The drape of claim 23 in which the one or more stays include a gantry second outer sidewall covering portion extending from the gantry inner wall covering portion.

26. The drape of claim 25 in which the gantry second outer sidewall covering portion includes an outer rim biased into a deployed shape and collapsible.

27. The drape of claim 23 further including means for removably attaching the gantry first outer sidewall covering portion to a first outer gantry sidewall.

28. The drape of claim 27 in which said means includes Velcro patches on the gantry first outer sidewall covering portion and corresponding Velcro patches on the first outer gantry sidewall.

29. The drape of claim 23 further including means for removably attaching the stays to a second outer gantry sidewall.

30. The drape of claim 29 in which the means for removably attaching the stays to the second outer gantry sidewall include a Velcro patch on each stay and corresponding Velcro patches on the second outer gantry sidewall.

31. The drape of claim 23 further including sleeves on the stays.

32. The drape of claim 23 further including sleeves on the gantry first outer sidewall covering portion.

33. The drape of claim 23 in which the stay holder is removably attached to the stays via Velcro on the stays and Velcro on the stay holder.

34. The drape of claim 23 in which the stay holder is ring shaped.

* * * * *